United States Patent [19]

Brown et al.

[11] Patent Number: 5,445,821

[45] Date of Patent: Aug. 29, 1995

[54] FRAGRANCE SAMPLER AND APPLICATOR WITH SIMULATED CONTAINER AND REMOVABLE CAP

[75] Inventors: Hubert F. Brown, Hixson; Paul J. A. French, Signal Mountain, both of Tenn.

[73] Assignee: Arcade, Inc., Chattanooga, Tenn.

[21] Appl. No.: 138,251

[22] Filed: Oct. 14, 1993

Related U.S. Application Data

[63] Continuation-in-part of Ser. No. 821,014, Jan. 15, 1992, abandoned.

[51] Int. Cl.$^6$ .......................... A61K 7/00; A61K 9/50
[52] U.S. Cl. ..................... 424/401; 424/496; 428/905; 428/916; 512/4
[58] Field of Search ............... 424/401, 490, 492, 496, 424/456; 428/905, 919; 514/4

[56] References Cited

U.S. PATENT DOCUMENTS

| | | | |
|---|---|---|---|
| 4,925,667 | 5/1990 | Fellows | 424/401 |
| 4,940,584 | 7/1990 | Tararus | 424/401 |
| 4,952,400 | 8/1990 | Tararuj | 424/401 |
| 5,050,910 | 9/1991 | Schechter | 428/905 |

Primary Examiner—Thurman K. Page
Assistant Examiner—Sally Gardner
Attorney, Agent, or Firm—Baker, Donelson, Bearman & Caldwell

[57] ABSTRACT

A fragrance sampler has an image of a perfume bottle printed on a paper sheet, the image including a body portion and a cap portion. The part of the sheet on which the cap is printed is removable from the rest of the sheet and is connected to a strip on which microcapsules enclosing droplets of the displayed perfume are adhered. The strip is located underneath the sheet on which the image is printed and is concealed from view until removed along with the cap portion. Effective light adhesion is provided by using gelatin-walled microcapsules, which adhere to the strip without use of binder when applied from an aqueous slurry. Upon detaching the cap portion and pulling it away from the sampler, the perfume-carrying strip is also removed, allowing the strip to be used as an applicator for placing sample particles on the skin of the user. The sampler effectively simulates the bottle used for a particular perfume and correlates the visual image of the bottle with a fragrance that is delivered.

14 Claims, 1 Drawing Sheet

FRAGRANCE SAMPLER AND APPLICATOR WITH SIMULATED CONTAINER AND REMOVABLE CAP

CROSS REFERENCE OF RELATED APPLICATION

This application is a continuation-in-part of application Ser. No. 07/821,014, filed on Jan. 15, 1992, now abandoned.

FIELD OF THE INVENTION

This invention relates generally to fragrance samplers and more particularly to printed samplers having fragrance-releasing material deposited on a substrate.

BACKGROUND OF THE INVENTION

Fragrance sampling devices in which fragrance-releasing material is carried on a substrate are widely used in advertising and promotion of perfumes and similar products. Such devices typically have very small droplets of perfume oil incorporated in microcapsules of rupturable wall material such as gelatin or urea-formaldehyde, with the microcapsules being deposited as a coating on a paper substrate of a magazine insert or direct mailer. To prevent premature release of the fragrance, coated areas of the substrate are enclosed in a removable cover sheet, which the recipient is encouraged to remove to gain access to the encapsulated product.

Microcapsules in such devices are typically contained in a layer of adhesive or binder having a greater cohesive strength than the microcapsule walls so that when the sheet bonded to the adhesive layer is pulled away, the microcapsule walls will be ruptured, producing an initial burst of fragrance. Further release of fragrance may then be obtained by scratching or rubbing the microcapsule-containing adhesive layer to rupture additional microcapsules.

Various sampler devices provided with a layer of rupturable microcapsules are disclosed in recent patents. U.S. Pat. No. 4,752,496, issued Jun. 21, 1988, to Fellows et al., discloses a sampler wherein powdered cosmetic material encapsulated and combined with a film-forming material is disposed as a coating on a non-removable substrate with a cover sheet aligned over the deposited coating. Adherence of the cosmetic coating to the substrate is controlled to permit the user to wipe it from the base sheet onto the user's skin. U.S. Pat. Nos. 4,940,584 and 4,952,400, issued Jul. 10, 1990, and Aug. 28, 1990, respectively, to Tararuj et al., disclose samplers having a layer of fragranced powder particles or mixtures thereof with perfume-containing microcapsules and a binder deposited on a substrate. U.S. Pat. No. 4,889,755, issued Dec. 26, 1989, to Charbonneau, discloses a sampler in which a removable strip coated with microcapsules is disposed between sheets and is adhered to at least one of the sheets by a binder or adhesive. Removal of the strip by pulling it ruptures at least some of the microcapsules providing a burst of fragrance. U.S. Pat. No. 4,988,557, issued Jan. 29, 1991, to the same inventor, discloses a fragrance sampler device wherein pull-apart sheets have a layer of microcapsules disposed between the sheets in two zones, one of which is strongly bonded so that the microcapsules in this zone will rupture upon pulling the sheets apart, and the other weakly bonded, the microcapsules in the second zone being rupturable by gentle rubbing.

Schechter et al. in U.S. Pat. No. 5,050,910, issued Sep. 24, 1991, disclose a fragrance-releasing magazine insert having a removable unit made up of four sheets, two of which are adhesively bonded to a layer containing rupturable microcapsules. A strong release of fragrance is obtained by pulling the two sheets apart after they have been separated from the insert as part of a removable unit. This patent also discloses an image of a perfume bottle and cap printed on the insert.

It is desired to provide a sampler having a removable strip with fragrance-containing microcapsules adhered to a surface thereof and arranged so that the strip may be detached and removed without initial rupture of substantial numbers of the microcapsules. This will minimize the initial fragrance burst upon removal of the strip, most of the fragrance being reserved for release after being applied to the skin of the user. Another desired feature of samplers of products sold in a distinctive or expensive container, for example, fine perfume in "designer" bottles, is to incorporate in a sampler a simulation or replica of the container and its cap or closure with a fragrance-containing strip attached to the cap. This would encourage the user, when provided with instructions on the sampler, to remove the cap and attached strip and employ the strip as an applicator for the product. The sampler should also be amenable to fabrication by mass production methods using high-speed printing equipment such as web printing processes.

SUMMARY OF THE INVENTION

The present invention is directed to a fragrance sampler having a removable strip with microcapsules that contain perfume lightly adhered to a surface of the strip, along with a powder diluent. The strip is located between two facing sheets of the sampler that form an enclosure, the strip being removable from between the sheets by pulling it out. Unlike the samplers disclosed in the patents referenced above, the strip is not adhesively bonded to an opposing sheet to a substantial extent at any area where the perfume-containing microcapsules are located. Thus, the initial burst of fragrance, obtained in prior samplers upon pulling a strip away from a sheet and thereby rupturing microcapsules contained in an adhesively bonded layer between these two parts, is avoided in the present invention. Instead of being ruptured, the lightly adhered microcapsules are available for being applied to the skin of a user, where they may be ruptured by gentle rubbing, providing a highly effective sampling mechanism.

Adhesion of the microcapsules to a surface of the strip, without forming a substantial bond to an opposing sheet surface, is provided by using gelatin-walled microcapsules and obtaining adhesion solely from the gelatin contained in the microcapsule walls, when deposed from an aqueous slurry. Adhesion to an opposing sheet surface is also prevented by inclusion of an inert powder diluent such as talc or kaolin mixed with the microcapsules. The microcapsule-powder slurry mixture is applied to the strip in production of the sampler in a manner such that drying of this deposited mixture on the strip is substantially complete before the mixture comes into contact with an opposing, folded-over sheet. Adhesion to the sheet is thereby minimized. Typically, only a small to negligible percentage of the microcapsules adhere to the opposing sheet.

The sampler may be made of coated paper, using high-speed printing equipment for application of printed images and the microcapsule-containing mixture, as well as for folding and providing perforations as required. A preferred sampler structure has top and bottom sheets with an image of a perfume bottle and other advertising material printed on the outside of the sheets, the microcapsule-carrying strip being provided as a cut-away portion of a folded-over end of one of the sheets. The folded-over end is located between the two sheets, and the top of the strip, above the deposited microcapsules, is adhesively connected to a removable tab cut into the top sheet. Pulling on this tab breaks perforations as required and enables removal of the strip. Adhesives without microcapsules are provided as required to secure the various sheets together around their peripheries away from the removable strip. The tab for grasping to remove the sampling strip may have an image of a cap or stopper printed on each face thereof to simulate opening of a bottle when the tab is pulled out, thus providing an effective attention-getting approach to inducing the user to actually apply the perfume product to the skin.

The invention provides another advantage in that samplers using the lightly adhered microcapsule-powder layer of the invention show a high resistance to leakage of fragrance due to damage during handling. Applicants have learned that samplers made according to the invention are the only microencapsulated samplers that have been found acceptable by the New York Times for inclusion as inserts in publications. The improved leakage resistance is believed to result from higher flexibility of the layer and a capability of particles in the layer to undergo some movement when subjected to action of mechanical rollers or the like.

It is, therefore, an object of this invention to provide a fragrance sampler carrying fragrance-releasing microcapsules in a manner such that the microcapsules may be removed from the sampler and applied to a user's skin with minimized initial fragrance burst.

Another object is to provide a fragrance sampler wherein fragrance-containing microcapsules are adhered to an applicator strip without being substantially adhered to a sheet in facing relation to the strip.

Another object is to provide a fragrance sampler that simulates the appearance of a container and induces a user to open the simulated container by removing a simulated cap.

Other objects and advantages of the invention will be apparent from the following detailed description and claims appended thereto.

DESCRIPTION OF THE PREFERRED EMBODIMENT

Figure 1:
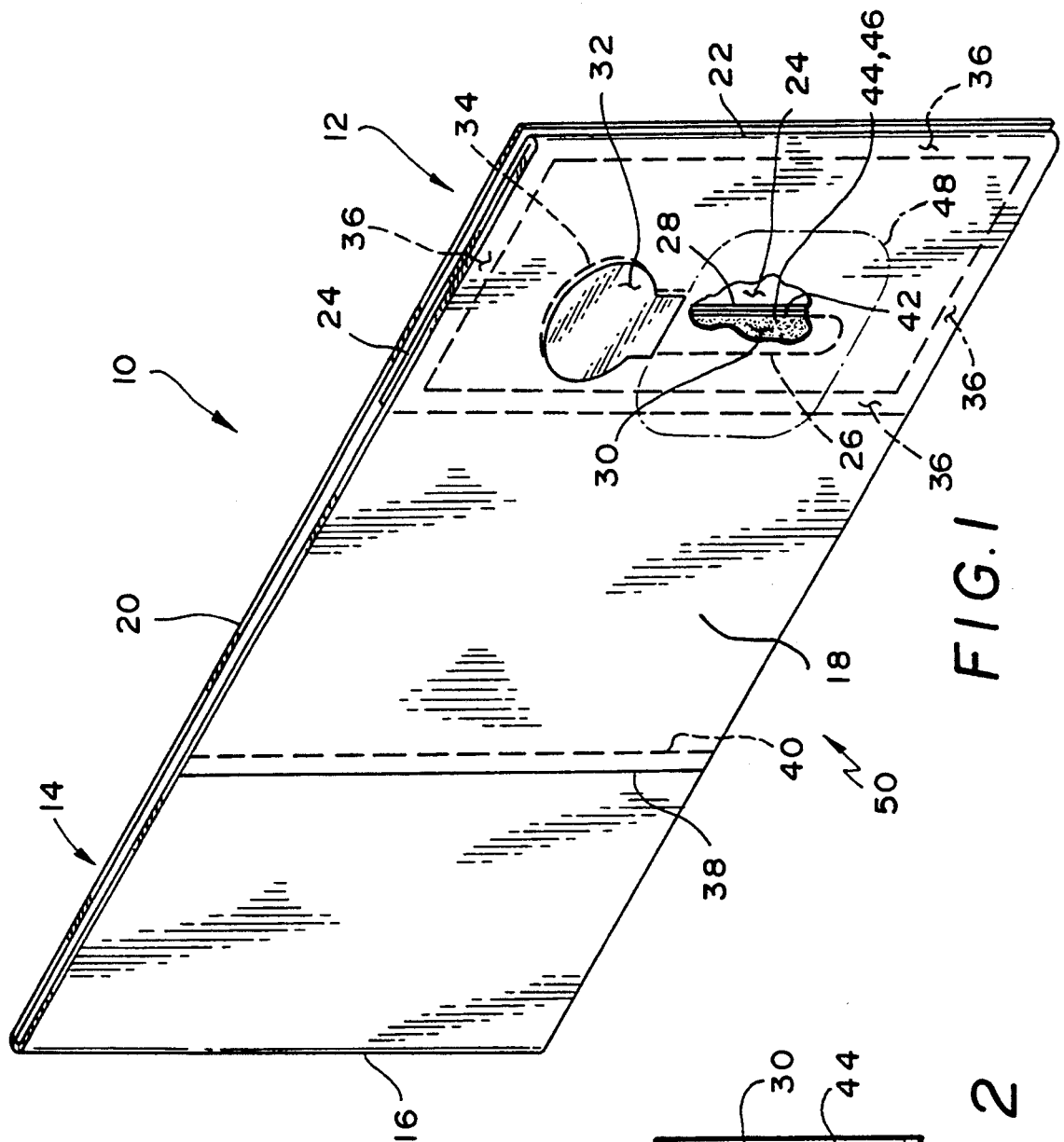
FIG. 1 is a perspective view of a sampler embodying the invention.
Figure 2:
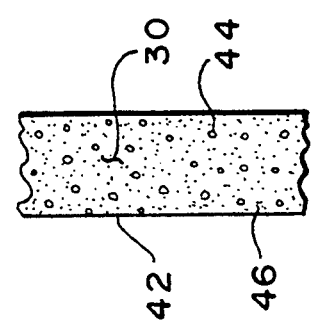
FIG. 2 is a cut-away view of a portion of the applicator strip showing a layer of a mixture of microcapsules and an inert powder diluent deposited thereon.

Referring to FIGS. 1 and 2 of the drawings, there is shown a magazine insert 10 having a sampler portion 12 and integral therewith a retainer portion 14 adapted to extend across the center line between pages of a magazine. The insert is made up of a single rectangular piece of coated paper folded over at end line 16 of retainer portion 14 to define a top sheet 18 and a facing bottom sheet 20. At line 22 defining the outer end of sample portion 12, top sheet 18 is folded over inwardly to provide a middle sheet 24 extending for about one-half the length of the sampler.

A strip 26 is defined in sheet 24 by a cut 28 extending around applicator surface 30 and cap image portion 32 integral with the applicator. Cap image portion 32 of sheet 24 is adhesively secured to removable cap image portion 34 cut in sheet 24. Strip 26 may be removed by grasping cap portion 34, breaking away any remaining connected portions at perforated areas and pulling the strip from between the top and bottom sheets.

Sheets 18 and 20 of the insert as well as middle sheet 24 are bonded to one another by a framework of adhesive edge strips 36, which may be comprised of conventional low-odor adhesive. The strips are spaced apart from the removable applicator strip so as not to interfere with the sampling operation.

The insert is creased along line 38 between the sampler and retainer portions and has a perforated line 40 parallel to and spaced apart from line 38 to enable the sampling portion to be torn out and removed from the magazine if desired.

Surface 30 of applicator strip 26 has deposited thereon a layer 42 of a mixture of fragrance-containing, gelatin-walled microcapsules 44 and an inert diluent powder 46. Preferably, the fragrance carried in the microcapsules would correspond to the brand depicted on bottle image 48.

In order to avoid a strong initial release of fragrance upon removing the strip from the sampler, the microcapsules, unlike those in prior samplers, are not located within an adhesive layer between two sheets that must be broken apart to provide access to the fragrance. Such action would necessarily rupture many of the microcapsules and give a strong initial burst of fragrance. Release of most of the fragrance from the present sampler is delayed until the user has removed the cap and attached strip and has brought the strip into contact with the skin to deposit the microcapsules. Gentle rubbing will then rupture the walls to release the bulk of the fragrance. Appropriate directions encouraging the recipient to follow such a procedure would be printed on the sampler. The cap or "stopper" removal procedure would provide an attention-getting feature, tending to induce on the part of the recipient a desire to perform the physical manipulations involved in accessing the product. The sampler, when used according to a prescribed procedure, would result in application of the fragrance to the user's skin, which is believed to be more effective in producing sales than merely smelling of the fragrance sample.

The fragrance-containing material of layer 42 preferably comprises gelatin-walled microcapsules enclosing very small droplets of perfume oil encased therein, with the microcapsules being lightly adhered to the substrate solely by adhesive action of the gelatin walls themselves when applied to the substrate from an aqueous slurry. No added adhesive or binder is required for the preferred gelatin microcapsules. The gelatin-walled microcapsules may be prepared by liquid bath encapsulation methods wherein perfume oil is emulsified by mixing with a gelatin solution in water, and the emulsion is combined with a coacervant such as an aqueous solution of gum arabic and a cross-linking agent which may be an aldehyde or organic titanate chelate as disclosed in co-pending application Serial No. 07/536,970, filed Jun. 12, 1990, for "Microcapsules and Method of Preparation," assigned to a common assignee. The encapsulated perfume oil droplets may also include a stabilizing amount of ethyl cellulose to prevent loss of more volatile components as disclosed in U.S. Pat. No. 5,051,305, issued Sep. 21, 1991, for "Stabilized Perfume-Containing Microcapsules and Method of Preparing the Same," also assigned to a common assignee. Microcapsules having walls made up of other polymeric material such as polyamides or urea-melamine-formaldehyde copolymers or the like as are known in the prior art may also be used. Such other materials, however, lack the natural adhesion of gelatin so that a small amount of adhesive would be required for lightly adhering the microcapsules to the substrate. In addition to perfume-containing microcapsules, layer 42 also includes in a mixture therewith an inert powder diluent such as talc or kaolin to prevent bonding of the layer to sheet 18 and to provide a lower level of adhesiveness to strip 26 and thus enable the mixture to be more readily removed upon contacting the substrate with the skin of a user. A powder mixture comprising talc or kaolin and microcapsules at a proportion of 1:1 to 3:1 and preferably 2:1 talc or kaolin in proportion to the microcapsules may be used. Other diluent powders may also be used in combination with microcapsules, in particular, powders of other inorganic clay materials, titanium dioxide, diatomaceous earth or the like, or organic materials such as starch or wax.

Samplers embodying the invention may be manufactured by conventional processes using high-speed printing equipment wherein the respective materials are applied as an aqueous slurry with sufficient fluidity to behave as an ink. Cuts and perforations in locations as described above may be made by use of suitable dies supported by rollers of the printing equipment. In preparation of a sampler as shown in the drawings, the sheet 50 is first fed through a printer so that images of the bottle 48 and cap 32, 34 as shown, along with any other graphic or written material, are imprinted on the sheet at locations as shown. After making such perforations, the slurry of microcapsules and powdered diluent is then applied to the applicator strip by transfer from a pattern gluer in a separate pass through the printer. Adhesive strips 36 may then be applied by a second pattern gluer at locations as shown to provide an effective seal for enclosing the microcapsules. The sheet is then folded over to bound the adhesive strips to the opposing portions of the sheet.

Although the invention is illustrated above with respect to fragrance samplers in which droplets of perfume oil are incorporated in microcapsules, the invention may also be embodied in samplers for other liquid products, in particular, repellants, medications, and the like. The image displayed on the sampler could be one associated or identified with the product, and a distinctive tab or other portion of the image could be used instead of a cap portion. It is further to be understood that other changes and modifications may be employed without departing from the spirit and scope of the invention.

We claim:

1. A fragrance sampler comprising:
   a single sheet folded along a first transverse line to form a top and a bottom layer, said top layer being folded inwardly along a second transverse line to form a middle layer between the top and bottom layers;
   an applicator strip cut from said middle layer and removably disposed between the top and bottom layers of said single sheet, said strip having a mixture of fragrance-containing, gelatin-walled microcapsules and an inert diluent powder deposited on a face of said strip;
   said mixture being adhered to said face solely by the adhesive properties of the gelatin in the walls of said microcapsules when deposited from an aqueous slurry, and said mixture being in contact with but substantially unbonded to an opposing surface of said top layer; and
   means for grasping said strip.

2. A sampler as defined in claim 1 wherein said mixture comprises 1 to 3 parts by weight of said inert powder diluent per one part by weight of said fragrance-containing microcapsules.

3. A sampler as defined in claim 2 wherein said powder is selected from the group consisting of talc and kaolin.

4. A sampler as defined in claim 1 wherein an image of a fragrance container is provided on an outside surface of said top layer, and an image of a cap for said container is provided on a removable portion of said top layer, said removable portion being adhesively connected to said applicator strip.

5. A sampler as defined in claim 1 which further comprises sealing means for securing said top, bottom, and middle layers together around the peripheries thereof.

6. A sampler as defined in claim 5 wherein said sealing means comprises strips of adhesive disposed between and in contact with said layers.

7. A sampler as defined in claim 1 wherein said single sheet comprises coated paper.

8. A sampler as defined in claim 2 wherein said inert powder diluent is provided at a weight proportion of two parts by weight of said powder diluent per one part of said microcapsules.

9. A fragrance sampler comprising:
   a top layer, a bottom layer, and a middle layer, said layers being formed from a single sheet by folding said sheet along first and second transverse lines to form an enclosure;
   said middle layer having defined therein an applicator strip disposed between said top layer and said bottom layer;
   said applicator strip being removable from between said top layer and said bottom layer by pulling the strip outward;
   said applicator strip having adhered to a first face thereof a mixture comprising fragrance-containing gelatin-walled microcapsules and an inert diluent powder, said mixture being in contact with but substantially unbonded to an opposing surface of said top layer;
   said mixture being adhered to said first face of said strip by adhesive means consisting of gelatin from walls of said microcapsules when deposited from an aqueous slurry;
   said applicator strip including a tab enabling removal of the strip from between the top and bottom layers; and
   said top, bottom, and middle layers of said sheet being bonded together by a framework of adhesive strips spaced apart from said applicator strip so that said adhesive strips do not interfere with the removal of said applicator strip.

10. A fragrance sampler as defined in claim 9 wherein the tab of said applicator strip is adhesively bonded to a removable portion of said top layer in facing relation to said tab.

11. A fragrance sampler as defined in claim 10 wherein said removable portion has imprinted thereon an image of a cap for a perfume container, and a fixed area adjacent to said image has imprinted thereon an image of a perfume container so that said cap and container provide an overall image of a closed perfume container.

12. A fragrance sampler as defined in claim 9 wherein adhesion of said mixture to an opposing surface of said top layer is avoided by allowing the mixture to dry before bringing it into contact with the opposing surface of said top layer.

13. A fragrance sampler as defined in claim 9 wherein said mixture comprises one to three parts by weight of a powder selected from the group consisting of talc and kaolin per one part microcapsules.

14. A fragrance sampler as defined in claim 9 wherein perforations are provided in said middle layer along lines defining the tab of said applicator strip.

* * * * *